United States Patent [19]

Moriya et al.

[11]  4,108,874

[45]  Aug. 22, 1978

[54] PRODUCTION OF MALEIC ANHYDRIDE

[75] Inventors: Koji Moriya; Itsuo Furuoya, both of Osaka, Japan

[73] Assignee: Takeda Chemical Industries, Ltd., Osaka, Japan

[21] Appl. No.: 560,802

[22] Filed: Mar. 21, 1975

[30]    Foreign Application Priority Data

Apr. 9, 1974 [JP]  Japan .................................. 49-40566
May 22, 1974 [JP]  Japan .................................. 49-58117

[51] Int. Cl.$^2$ ......................................... C07D 307/60
[52] U.S. Cl. ................................. 260/346.75; 252/437
[58] Field of Search ....................... 260/346.8; 252/437

[56]              References Cited
                U.S. PATENT DOCUMENTS

| | | | |
|---|---|---|---|
| 3,156,705 | 11/1964 | Kerr | 260/346.8 |
| 3,793,225 | 2/1974 | Bertus et al. | 252/437 |
| 3,888,886 | 6/1975 | Young et al. | 260/346.8 |
| 3,899,516 | 8/1975 | Dickason | 260/346.8 |

FOREIGN PATENT DOCUMENTS

| | | | |
|---|---|---|---|
| 2,255,394 | 8/1973 | Fed. Rep. of Germany | 260/346.8 |
| 145,571 | 6/1962 | U.S.S.R. | 260/346.8 |

OTHER PUBLICATIONS

Handbook of Chemistry & Physics -Chem. Rubber Publish. Co., Cleveland, (1961), pp. 668-669.
Moeller, Inorganic Chemistry, John Wiley Publish. Co., (1952), p. 961.

*Primary Examiner*—Henry R. Jiles
*Assistant Examiner*—Bernard Dentz
*Attorney, Agent, or Firm*—Wenderoth, Lind & Ponack

[57]              ABSTRACT

Maleic anhydride is obtained in a high yield as well as in a high purity by oxidation of a hydrocarbon of not less than four carbon atoms in gaseous phase in the presence of a catalyst comprising (a) vanadium oxide, (b) phosphorus oxide, (c) thallium oxide and/or alkaline earth metal oxide, and if necessary, further containing (d) iron oxide.

2 Claims, No Drawings

PRODUCTION OF MALEIC ANHYDRIDE

The present invention relates to a method for the production of maleic anhydride. More specifically, the invention relates to a method for the production of maleic anhydride by oxidation of a hydrocarbon of not less than four carbon atoms in gaseous phase in the presence of a catalyst comprising (a) vanadium oxide, (b) phosphorus oxide, (c) thallium oxide and/or alkaline earth metal oxide, and if necessary, further containing (d) iron oxide.

Heretofore, in the production of maleic anhydride by catalytic oxidation of hydrocarbons of not less than four carbon atoms such as butane, butene-1, butene-2, butadiene, cyclopentadiene, benzene and hydrocarbon materials containing them (e.g. BB fraction, spent BB fraction, etc.), it was known to employ a catalyst composed of vanadium oxide and phosphorus oxide or a catalyst comprising, in addition to vanadium and phosphorus components, a third component such as lithium oxide, iron oxide, copper oxide or chromium oxide. However, with these catalysts, the yields and purities of the product have not been fully satisfactory, especially when a hydrocarbon material including butane, for example, spent BB fraction, spent-spent BB fraction, etc. is used.

To obviate these disadvantages we conducted intensive research, and have found that the above disadvantages are removed by employing thallium oxide and/or alkaline earth metal oxide as a third component in addition to vanadium oxide and phosphorus oxide, that is by employing a catalyst which comprises vanadium oxide, phosphorus oxide, thallium oxide and/or alkaline earth metal oxide, and if necessary further containing iron oxide. The present invention is accomplished on the basis of these new findings.

It is an object of the present invention to provide an industrially feasible method for the production of maleic anhydride in a high yield as well as in a high purity by oxidation of a hydrocarbon of not less than four carbon atoms in gaseous phase.

Another object of the present invention is to provide a novel, highly active and long-life catalyst useful for the production of maleic anhydride in a high yield as well as in a high purity by oxidation of a hydrocarbon of not less than four carbon atoms in gaseous phase.

Other objects will be apparent hereinafter.

The catalyst used according to the present invention comprises, as active ingredients, any of a compound oxide or a mixture of vanadium oxide, alkaline earth metal oxide and phosphorus oxide; a compound oxide or mixture of vanadium oxide, thallium oxide and phosphorus oxide; a compound oxide or mixture of vanadium oxide, alkaline earth metal oxide, phosphorus oxide and thallium oxide; a compound oxide or mixture of vanadium oxide, alkaline earth metal oxide, phosphorus oxide and iron oxide; a compound oxide or mixture of vanadium oxide, phosphorus oxide, thallium oxide and iron oxide; or a compound oxide or mixture of vanadium oxide, alkaline earth metal oxide, phosphorus oxide, thallium oxide and iron oxide; and usually, each of these compound oxides or mixtures is used as supported on a carrier.

The catalyst to be employed in the practice of the present invention can be prepared by procedures known per se for the manufacture of solid catalysts, one of which, for example, may be as follows.

Thus, a vanadium-containing compound, a phosphorus-containing compound, a thallium-containing compound and/or an alkaline earth metal-containing compound, and, if required, an iron-containing compound, each of which can be converted to the corresponding oxide by heating or through a chemical reaction, are dissolved, as required, in a suitable solvent such as water or alcohol, and a carrier is impregnated with the resulting solution or solutions. The impregnated carrier (catalyst intermediate) is then calcined at 300° to 800° C, preferably to 400° to 600° C, for 1 to 20 hours, preferably 2 to 10 hours.

As the aforementioned vanadium-containing compound, there may be mentioned vanadium oxides ($V_2O_5$, $V_2O_4$, $V_2O_3$, etc.), vanadates ($NH_4VO_3$, vanadyl oxalate, vanadyl sulfate, vanadyl chloride, etc.) and so on. As said phosphorus-containing compound, there may be mentioned phosphorus oxides ($P_2O_5$, $P_2O_3$, etc.), phosphoric acids ($HPO_3$, $H_3PO_4$, $H_4P_2O_7$, $H_3PO_3$, etc.), phosphates (($NH_4)_3PO_4$, $(NH_4)_2HPO_4$, $(NH_4)H_2PO_4$, etc.), phosphorus halides ($PCl_3$, $PCl_5$, $PBr_3$, etc.) and so on. As the thallium-containing compound, there may be mentioned thallium oxides ($Tl_2O$, $Tl_2O_3$), thallium nitrates, thallium halides (TlCl, $TlCl_3.4H_2O$, $TlF_3$, TlBr, $TlBr_3.4H_2O$, TlI, $TlI_3$, etc.), thallium sulfates ($Tl_2SO_4$, $Tl_2(SO_4)_3.7H_2O$), thallium carbonate, organic acid thallium salts (e.g. Tl(HCOO), Tl($CH_3$COO), $CH_2$(COOTl)$_2$,) and so on. The aforementioned alkaline earth metal-containing compound is exemplified by alkaline earth metal salts (nitrates, e.g. beryllium nitrate, magnesium nitrate, calcium nitrate, strontium nitrate, barium nitrate, radium nitrate; halides, e.g. magnesium chloride, calcium chloride, barium chloride carbonates, e.g. magnesium carbonate, strontium carbonate, barium carbonate; sulfates, e.g. calcium sulfate, barium sulfate; organic acid salts, e.g. magnesium acetate, calcium acetate; and so on), alkaline earth metal hydroxides (e.g. magnesium hydroxide, calcium hydroxide, strontium hydroxide, barium hydroxide), alkaline earth metal oxides (e.g. beryllium oxide, magnesium oxide calcium oxide, strontium oxide, barium oxide, radium oxide) and so on.

As the aforementioned iron-containing compound, there may be mentioned iron oxides ($Fe_2O_3$, $Fe_3O_4$), iron hydroxides (Fe(OH)$_3$, Fe(OH)$_2$), iron nitrates (Fe(NO$_3$)$_2$.9H$_2$O, Fe(NO$_3$)$_2$.6H$_2$O), iron chlorides (e.g. FeCl$_3$.6H$_2$O, FeCl$_2$.nH$_2$O), iron alums, iron sulfates (e.g. Fe$_2$(SO$_4$)$_3$.nH$_2$O), organic acid iron salts (e.g. FeC$_4$H$_2$O$_4$, FeC$_2$O$_4$.2H$_2$O), iron phosphates (FePO$_4$.nH$_2$O, Fe$_3$(PO$_4$)$_2$.8H$_2$O) and so on. Thus, in each instance, oxides or compounds which can be easily converted to oxides are employed.

In the manufacture of the catalyst to be employed in the practice of the present invention, the proportions of said vanadium-containing compound, phosphorus-containing compound, thallium-containing compound and alkaline earth metal-containing compound may be varied, although the atomic ratio of vanadium to phosphorus is preferably 2:1 to 1:10 and, for still better results, 1:1 to 1:5, and the atomic ratio of vanadium to thallium is preferably 1:5 to 100:1 and, for still better results, 1:2 to 20:1. The atomic ratio of vanadium to alkaline earth metal is 1:10 to 40:1 and, for still better results, 1:5 to 15:1. When the catalyst contains iron as well, the atomic ratio of vanadium to iron is preferably 1:5 to 100:1 and, for still better results, 1:2 to 20:1.

As for the carrier material, heat-resistant inorganic compounds such as, alumina, silicon carbide, titanium oxide, silica, magnesia, diatomaceous earth, pumice, zirconia, cerium oxide, titanium phosphate, aluminum phosphate, silicon phosphate, gypsum and their mixtures may be desirably employed. While the amount of catalytically active components to be supported depends upon the particular type of carrier material and the method of preparing the catalyst, among other conditions, it is usually not less than 3 percent by weight and, preferably, not less than 10 percent by weight.

The method for manufacturing the catalyst to be employed for the purposes of the present invention will be further described in detail. Thus, for example, to finely divided ammonium metavanadate is added water and, then, oxalic acid is further added to the mixture to prepare a homogeneous solution. Then, an aqueous solution of phosphoric acid and an aqueous solution of thallium nitrate and/or an alkaline earth metal hydroxide are added.

If necessary, an aqueous solution of ferric nitrate is further added. The above procedure is followed by the addition of a carrier material as suitably molded or in powdery form. The moisture is expelled on a hot water bath and, after evaporation to dryness, the mixture is calcined at a temperature of about 500° C.

As the hydrocarbon containing four or more carbon atoms which is employed in the production of maleic anhydride, there may be mentioned such materials as butane, butene-1, butene-2, butadiene, BB fraction, spent BB fraction, spent-spent BB fraction, cyclopentadiene, benzene and so on. Among the above, the hydrocarbon consisting essentially of four carbon atoms such as butane, butene-1, butene-2, butadiene, BB fraction, spent BB fraction, and spent-spent BB fraction is particularly preferable. As the oxidizing agent to be used for oxidizing such a starting material hydrocarbon, any oxygen-containing gas may be employed, and preferably air is usually employed as such an oxygen-containing gas, although oxygen itself or a mixture of air and oxygen, for instance, may also be employed.

The reaction temperature varies with the composition of the catalyst, the type of carrier material and other conditions, but usually the range of 250° to 650° C, or particularly the range of 300° to 550° C, is preferred. The mixing ratio of said starting material hydrocarbon to air or oxygen is of course preferably outside the explosion limits. More particularly, when air is used as a source of oxygen, 0.5 to 1.5 mole percent of hydrocarbon is preferably employed per mole of air. The material gas is contacted with the catalyst usually at a space velocity (converted to normal temperature and pressure) of 500 to 30,000 ($hr^{-1}$) and, preferably, at a space velocity of 1,000 to 10,000 ($hr^{-1}$). Under certain circumstances, the unreacted hydrocarbon may be recycled.

The product maleic anhydride is first trapped with a solvent such as, for example water and then can be purified by dehydration, distillation or other procedure. In this manner, a high purity grade of maleic anhydride can be obtained.

The present invention provides the advantages of:
(1) a high reaction yield;
(2) a minimum amount of byproduct monocarboxylic acid;
(3) a high yield even when the concentration of hydrocarbon in air is high; and
(4) a high yield even when a hydrocarbon material including butane is used as a starting material;

and also enables an increase in the space-time yield (STY) more easily than has been possible with the prior art method, in addition to the increased amenability to purification which provides for a more economical production of maleic anhydride in high purity.

The following examples are intended to further describe the present invention. It should, however, be understood that the available methods for manufacturing the catalyst are not limited to those set forth in the examples but any suitable method may be adopted within the framework of the invention thus far described.

In the examples, "part(s)" means "weight part(s)", unless otherwise specified.

EXAMPLE 1

In 500 parts of water was suspended 14.6 parts of ammonium metavanadate, followed by the addition of 23.6 parts of oxalic acid to prepare a homogeneous solution. To this solution were added 36.0 parts of an aqueous solution (85%) of orthophosphoric acid and 13.2 parts of strontium nitrate. After dissolution, the solution was used to impregnate 300 parts of a molded α-alumina carrier. Under stirring on a hot-water bath, the catalyst solution was evaporated to dryness on the carrier material.

The resulting composition was dried at 100° C overnight and then calcined in the air at 500° C for 4 hours to prepare a catalyst.

The above catalyst was packed into a conventional continuous fixed-bed reactor and a mixed gas of butene-1 and air(butene-1:1 mole %) was introduced at atmospheric pressure, a constant reactor bath temperature of 390° C and a space velocity (SV) of 5000($hr^{-1}$).

The conversion of butene-1 was 99 mole % and the yield of maleic anhyride was 56 mole %, while the yield of monocarboxylic acid was 1.7 mole %.

EXAMPLE 2

In the manufacture of a catalyst according to Example 1, 19.7 parts of barium hydroxide was used in place of 13.2 parts of strontium nitrate.

Using the resulting catalyst, the reaction was carried out under the same conditions as set forth in Example 1. The conversion of butene-1 was 100 mole %; yield of maleic anhydride was 58 mole %; and yield of monocarboxylic acid was 1.3 mole %.

EXAMPLE 3

In the manufacture of a catalyst according to Example 1, 9.2 parts of calcium chloride (dihydrate) was used in place of 13.2 parts of strontium nitrate. Using the catalyst thus obtained, the reaction was carried out under the same conditions as set forth in Example 1. In this instance, the conversion of butene-1 was 100 mole %; yield of maleic anhydride was 53 mole %; and yield of monocarboxylic acid was 2.7 mole %.

EXAMPLES 4 AND 5

In the manufacture of a catalyst according to Example 1, one of the alkaline earth metal salts mentioned in the following table was used in place of 13.2 parts of strontium nitrate. Using such catalysts, reactions were carried out in the same manner as Example 1. The results are set out in the extreme right column of the following table.

Table 1

| Example | The alkaline earth metal salt used and its amount | Yield of maleic anhydride |
|---|---|---|
| 4 | 16.0 parts of magnesium nitrate | 51 mole % |
| 5 | 10.0 parts of 50 wt. % aqueous solution of beryllium nitrate | 56 mole % |

EXAMPLES 6 TO 8

In Examples 6 to 8, an evaluation was made of the catalyst characteristics obtainable when the amount of BaO relative to the vanadium oxide-phosphorus oxide system was varied.

The procedure of Example 1 was repeated except that barium hydroxide, instead of strontium nitrate, was used in the amounts indicated in the following table to prepare catalysts. Using each of these catalysts, the reaction was carried out under the same conditions as set forth in Example 1. The results are shown in the extreme right column of the same table. The result obtained using a barium oxide-free catalyst is also shown as a control.

Table 2

| Example | Amount of BaO V : P : Ba (atomic ratio) | Yield of maleic anhydride (mole %) | Yield of monocarboxylic acid (mole %) |
|---|---|---|---|
| 6 | 1:2.5:0.1 | 59 | 1.3 |
| 7 | 1:2.5:0.2 | 58 | 1.2 |
| 8 | 1:2.5:1.0 | 53 | 1.5 |
| (1) | 1:2.5:0.5 | 56 | 1.7 |
| Control | 1:2.5:0 | 48 | 4.5 |

EXAMPLES 9 TO 11

In 236.0 parts of a 10% aqueous solution of oxalic acid was dissolved 14.6 parts of ammonium metavanadate, followed by the addition of 36.0 parts of aqueous orthophosphoric acid (85%) and 16.3 parts of barium nitrate.

In the mixture was immersed 400 parts of a molded α-alumina carrier, about 5 mm by 5 mm, and under occasional stirring on a hot-water bath, the catalyst solution was evaporated to dryness on the carrier. After drying at 100° C, the catalyst intermediate was calcined at 450° C for 5 hours to prepare a catalyst. Using this catalyst, the reaction was carried out under the same conditions as Example 1 except that the mixing ratio of butene-1 with air was varied as shown in the following table.

The results are set forth in the extreme right column of the same table.

Table 3

| Example | Concentration of butene-1, mole % relative to air | Yield of maleic anhydride (mole %) |
|---|---|---|
| 9 | 0.5 | 58 |
| 10 | 1.0 | 57 |
| 11 | 1.5 | 58 |

EXAMPLE 12

In 360 parts of a 20% aqueous solution of phosphoric acid was dissolved 24.3 parts of ammonium metavanadate, followed by the addition of 400 parts of a 10% aqueous solution of oxalic acid. To the mixture was added 66.7 parts of barium hydroxide and while the entire mixture was stirred, 500 parts of titanium oxide power was immersed therein. The moisture was expelled on a hot-water bath until a paste was obtained. The paste was extruded and granulated to spheres about 4 mm in diameter. After drying, the spherical granules were calcined at 500° C for 4 hours to prepare a catalyst. Using this catalyst, the reaction was carried out under the same conditions as Example 1 except that the reactor bath temperature was 380° C. The conversion of butene-1 was 100 mole %; yield of maleic anhydride was 58 mole %; and yield of monocarboxylic acid was 1.6 mole %.

EXAMPLE 13

In 245 parts of a 20% aqueous solution of phosphoric acid was dissolved 14.6 parts of ammonium metavanadate, followed by the addition of 240 parts of a 10% aqueous solution of oxalic acid.

The above procedure was further followed by the addition of 33.2 parts of strontium hydroxide. Then, 400 parts of α-alumina powder, about 1 μ in diameter, was immersed in the resulting mixture.

The composition was then treated on a hot-water bath to prepare a paste.

Following the addition of 40 parts of starch, the paste was extruded and then granulated to spheres about 4mm in diameter. After drying, the granules were calcined at 550° C for 3 hours to prepare a catalyst. Using this catalyst, the reaction was carried out under the same conditions as Example 1. The conversion of butene-1 was 97 mole %; yield of maleic anhydride was 55 mole %; and yield of monocarboxylic acid was 3.4 mole %.

EXAMPLES 14 THROUGH 20

Using the catalyst prepared in Example 2, the hydrocarbon materials indicated in the following table were reacted in the same manner as Example 1. The results are set forth in the extreme right column of the same table.

Table 4

| Example | Hydrocarbon material | Yield of maleic anhydride (mole %) |
|---|---|---|
| 14 | cis-Butene-2 | 57 |
| 15 | trans-Butene-2 | 58 |
| 16 | Butadiene | 66 |
| 17 | Cyclopentadiene | 55 |
| 18 | Benzene | 55 |
| 19 | Spent BB fraction[1] | 26 |
| 20 | Spent-spent BB fraction[2] | 50 |

[1]Butene 39%, isobutene, 52%, butanes, etc. 9%
[2]Butene 81%, butanes, etc. 19%

EXAMPLES 21 AND 22

Using the catalyst according to Example 12, mixed gases of butane and air (butane: 1 mole % and 1.5 mole %, respectively) were reacted at atmospheric pressure, a constant reactor bath temperature of 480° C and a space velocity (SV) of 2000 (hr$^{-1}$). The results are set forth in the following table.

Table 5

| Example | Concentration of butane (mole % relative to air) | Yield of maleic anhydride (mole %) |
|---|---|---|
| 21 | 1 | 38 |
| 22 | 1.5 | 39 |

EXAMPLE 23

In 480 parts of a 5% aqueous solution of oxalic acid was dissolved 14.6 parts of ammonium metavanadate, followed by the addition of 43.2 parts of aqueous orthophosphoric acid (85%), 13.2 parts of strontium nitrate and 10.1 parts of ferric nitrate. To this mixed solution was added 300 parts of titanium oxide powder and a portion of the water was expelled on a hot water bath until a paste was obtained. The paste was extruded into cylinders, about 2 mm by 5 mm. After drying, the cylinders were calcined at 500° C for 4 hours to prepare a catalyst. Using this catalyst, a mixed gas of butane and air (butane: 1 mole %) was reacted at atmospheric pressure, a constant reaction bath temperature of 470° C and a space velocity (SV) of 3000 $(hr^{-1})$. The yield of maleic anhydride was 38 mole %.

EXAMPLE 24

In the preparation of the catalyst according to Example 23, 8.85 parts of calcium nitrate was used in place of 13.2 parts of strontium nitrate. Using this catalyst, the reaction was carried out under the same conditions as Example 23.

The yield of maleic anhydride was 35 mole %.

EXAMPLE 25

In the preparation of a catalyst according to Example 23, 16.3 parts of barium nitrate was used in place of 13.2 parts of strontium nitrate. Using the resulting catalyst, the reaction was carried out under the same conditions as Example 23. The yield of maleic anhydride was 40 mole %.

EXAMPLE 26

In 500 parts of a 5% aqueous solution of oxalic acid was dissolved 14.6 parts of ammonium metavanadate, followed by the addition of 36.0 parts of aqueous orthophosphoric acid (85%), 15.8 parts of barium hydroxide and 6.6 parts of thallium nitrate. Thereafter, the procedure of Example 23 was followed to prepare a catalyst. Using this catalyst, the reaction was carried out under the same conditions as Example 1. The conversion of butene-1 was 100 mole %; yield of maleic anhydride was 62 mole %; and yield of monocarboxylic acid was 0.9 mole %.

EXAMPLE 27

In the preparation of a catalyst according to Example 26, 10.0 parts of strontium hydroxide was used in place of 15.8 parts of barium hydroxide. Using the resulting catalyst, the reaction was carried out under the same conditions as Example 1. The conversion of butene was 100 mole %; yield of maleic anhydride was 61 mole %; and yield of monocarboxylic acid was 1.1 mole %.

EXAMPLE 28

In 500 parts of a 5% aqueous solution of oxalic acid was dissolved 14.6 parts of ammonium metavanadate, followed by the addition of 43.2 parts of aqueous orthophosphoric acid (85%), 19.7 parts of barium hydroxide, 3.3 parts of thallium nitrate and 10.1 parts of ferric nitrate.

Thereafter, the procedure of Example 23 was followed to prepare a catalyst. Using this catalyst, the reaction was carried out under the same conditions as Example 23. The yield of maleic anhydride was 42 mole %.

EXAMPLE 29

In 500 parts of water was suspended 14.6 parts of ammonium metavanadate, followed by the addition of 23.6 parts of oxalic acid to prepare a homogeneous solution. To this solution were added 36.0 parts of an aqueous solution (85%) of orthophosphoric acid and 19.7 parts of barium hydroxide. After dissolution, the solution was used to impregnate 300 parts of titanium phosphate powder ($TiO_2/P_2O_5$ mole ratio = 5:2). Under stirring on a hot-water bath, the catalyst solution was evaporated to prepare a paste.

The paste was extruded into cylinders about 2 mm by 5 mm. After drying, the cylinders were calcined at 500° C for 5 hours to prepare a catalyst. Using this catalyst, the reaction was carried out under the same conditions as Example 1.

The conversion of butene-1 was 100 mole %; yield of maleic anhydride was 58 mole %; and yield of monocarboxylic acid was 2.1 mole %.

EXAMPLE 30

In 500 parts of water was suspended 14.6 parts of ammonium metavanadate, followed by the addition of 23.6 parts of oxalic acid to prepare a homogeneous solution. To this solution were added 16.7 parts of thallium nitrate and 36.0 parts of aqueous orthophosphoric acid (85%). After dissolution, 300 parts of molded $\alpha$-alumina was immersed in the solution and, under occasional stirring on a hot-water bath, the catalyst-solution was evaporated to dryness on the $\alpha$-alumina carrier. After drying at 100° C overnight, the composition was calcined in the air at 450° C for 4 hours to prepare a catalyst.

This catalyst was packed into a conventional continuous fixed-bed reactor, in which a mixed gas of butene-1 and air (butene-1:1 mole %) was reacted at atmospheric pressure, a reactor bath temperature of 400° C and a space velocity (SV) of 5000 $(hr^{-1})$. The conversion of butene-1 was 98% and the yield of maleic anhydride was 58 mole %, while the yield of monocarboxylic acid was 1.3 mole %.

EXAMPLES 31 THROUGH 33

Using the catalyst according to Example 30, the reaction was carried out under the same conditions as Example 30 except that the concentration of hydrocarbon in air was varied as shown in the following table. The results are set forth in the same table.

Table 6

| Example | Butene-1/air (mole %) | Yield of maleic anhydride (mole %) |
| --- | --- | --- |
| 31 | 0.5 | 59 |
| 32 | 1.2 | 58 |
| 33 | 1.5 | 56 |

EXAMPLE 34

In 800 parts of water was suspended 21.9 parts of ammonium metavanadate, followed by the addition of 35.4 parts of oxalic acid to prepare a homogeneous solution. In this solution were dissolved 64.8 parts of phosphoric acid (85% aqueous solution) and 10.1 parts of thallium nitrate. The resultant solution was used to impregnate titanium oxide granules, 7 to 10 meshes, and under occasional stirring on a hot-water bath, the catalyst-solution was evaporated to dryness on the carrier.

After drying at 100° C, the composition was calcined at 450° C for 5 hours. Using this catalyst, the reaction was carried out under the same conditions as Example 30. In this example, the conversion of butene-1 was 100% and the yield of maleic anhydride was 60 mole %. The yield of monocarboxylic acid was less than 1 mole %.

EXAMPLES 35 THROUGH 41

Using the catalyst according to Example 34, the reaction was carried out in the same manner as Example 30 except that the hydrocarbons indicated in the following table were used in place of butene-1. The results are set forth in the same table.

Table 7

| Example | Raw material | Yield of maleic anhydride (mole %) |
|---|---|---|
| 35 | cis-Butene-2 | 60 |
| 36 | trans-Butene-2 | 59 |
| 37 | Butadiene | 65 |
| 38 | Spent BB fraction[1] | 27 |
| 39 | Spent-spent BB fraction[2] | 51 |
| 40 | Cyclopentadiene | 58 |
| 41 | Benzene | 58 |

[1]Butene 39%; isobutene 52%; butane, etc. 9%
[2]Butene 81%; butane, etc. 19%

EXAMPLE 42

In 500 parts of a 5% aqueous solution of oxalic acid was dissolved 14.6 parts of ammonium metavanadate, followed by the addition of 22.2 parts of phosphorus pentoxide, 16.7 parts of thallium nitrate, and 5.1 parts of ferric nitrate. The resulting mixed solution was used to impregnate 300 parts of α-alumina powder and a portion of the water was evaporated off to leave a paste.

The paste was extruded and sphered about 4 mm in diameter. After drying, the spheres were calcined in the air at 500° C for 4 hours to prepare a catalyst. Using this catalyst, the reaction was carried out under the same conditions as Example 30 except that the reaction temperature was 460° C. The conversion of butene-1 was 100%; yield of maleic anhydride was 56 mole %; and yield of monocaboxylic acid was 3 mole %.

EXAMPLE 43

In 600 parts of a 5% aqueous solution of oxalic acid was dissolved 17.5 parts of ammonium metavanadate, followed by the addition of 79.3 parts of diammonium phosphate and 20.0 parts of thallium nitrate. To this solution was added 350 parts of finely divided titanium oxide (reagent grade #1), and the water was evaporated off to prepare a paste, which was then wet-granulated. After drying, the granules were calcined in the air at 500° C for 3 hours.

The reaction was carried out under the same conditions as Example 30.

The conversion of butene-1 was 100%; yield of maleic anhydride was 58 mole %; and yield of monocarboxylic acid was 2 mole %.

EXAMPLE 44

In 500 parts of a 10% aqueous solution of oxalic acid was dissolved 30 parts of ammonium metavanadate, followed by the addition of 70 parts of aqueous orthophosphoric acid and 13 parts of thallium nitrate. To the resulting homogeneous solution was added 400 parts of finely divided titanium oxide and the water was evaporated off on a hot-water bath. When the system had become viscous, a small amount of water was added. The composition was placed on a flat plate where it was dried. The dried composition was crushed and sieved to 7–10 meshes, after which it was heat-treated in the air at 550° C for 3 hours to prepare a catalyst.

This catalyst was packed into the same reactor as that used in Example 30 and a mixed gas of n-butane and air (butane: 1 mole %) was reacted at atmospheric pressure, a space velocity (SV) of 2000 ($hr^{-1}$) and a reaction temperature of 515° C.

The conversion of butane was 72 mole %; yield of maleic anhydride was 35 mole %; and yield of monocarboxylic acid was 1.4 mole %.

EXAMPLE 45

Using the catalyst of Example 44, the reaction was carried out with a mixing ratio of n-butane to air of 1.5 mole % at a reaction temperature of 525° C and a space velocity (SV) of 3000 ($hr^{-1}$). In this example, the conversion of butane was 83 mole %; yield of maleic anhydride was 34 mole %; and yield of monocarboxylic acid was 0.8 mole %.

EXAMPLE 46

In 1000 parts of water was suspended 30 parts of ammonium metavanadate, followed by the addition of 50 parts of oxalic acid and 90 parts of aqueous phosphoric acid (85%). After a homogeneous solution was prepared, 13 parts of thallium nitrate and 20 parts of ferric nitrate were added. To this solution containing catalyst-active components was added 400 parts of titanium oxide powder in the size range of 10 to 20 meshes and the composition was evaporated to dryness on a hot-water bath. After drying, the composition was calcined at 500° C for 5 hours to prepare a catalyst.

Using this catalyst, a mixed material gas of n-butane and air (n-butane: 1.2 mole %) was reacted at a space velocity (SV) of 2000 ($hr^{-1}$) and a reaction temperature of 510° C. The conversion of butane was 81 mole %; yield of maleic anhydride was 37 mole %; yield of monocarboxylic acid was 1.1 mole %.

EXAMPLE 47

Using the same catalyst as that used in Example 46, air containing 1.2 mole % of n-butane was reacted at a space velocity (SV) of 3000 ($hr^{-1}$) and a reaction temperature of 506° C.

The conversion of butane was 51 mole %; yield of maleic anhydride was 27 mole %; and yield of monocarboxylic acid was 0.6%.

EXAMPLE 48

In 500 parts of a 10% aqueous solution of oxalic acid was dissolved 30 parts of ammonium metavanadate, followed by the addition of 70 parts of aqueous orthophosphoric acid (85%) and 13 parts of thallium nitrate. To this solution was added 400 parts of titanium phosphate powder ($TiO_2/P_2O_5$ mole ratio=1:1).

Under stirring on a hot-water bath, the catalyst solution was evaporated to prepare a paste. The paste was extruded into cylinders about 2 mm by 5 mm. After drying, the cylinders were calcined at 500° C for 5 hours to prepare a catalyst. Using this catalyst, the reaction was carried out under the same conditions as Example 30.

The conversion of butene-1 was 100 mole %; yield of maleic anhydride was 60 mole %; and yield of monocarboxylic acid was 2.6 mole %.

What is claimed is:

1. In a method for producing maleic anhydride by oxidation of a hydrocarbon having not less than four carbon atoms in gaseous phase in the presence of a catalyst, the improvement wherein the catalyst comprises (a) vanadium oxide, (b) phosphorus oxide and (c), thallium oxide the amount of vanadium oxide relative to phosphorus oxide being from about 1:1 to about 1:5 based on the atomic ratio of vanadium to phosphorus, the amount of vanadium oxide relative to thallium oxide, being from about 1:2 to about 20:1 based on the atomic ratio of vanadium to thallium.

2. A method as claimed in claim 1, wherein the hydrocarbon consists essentially of four carbon atoms.